(12) United States Patent
Holm et al.

(10) Patent No.: US 12,157,905 B2
(45) Date of Patent: Dec. 3, 2024

(54) CRISPR GENE THERAPY OF FUSION GENE RELATED CANCERS

(71) Applicant: Aarhus Universitet, Aarhus C (DK)

(72) Inventors: Christian Kanstrup Holm, Lystrup (DK); Yonglun Luo, Egå (DK); Magnus Stougaard, Viby J (DK); Charlotte Thornild Møller, Lystrup (DK); Mette Nyegaard, Gistrup (DK)

(73) Assignee: Aarhus Universitet, Aarhus (DK)

(*) Notice: Subject to any disclaimer, the term of this patent is extended or adjusted under 35 U.S.C. 154(b) by 748 days.

(21) Appl. No.: 17/312,808

(22) PCT Filed: Dec. 18, 2019

(86) PCT No.: PCT/EP2019/085957
§ 371 (c)(1),
(2) Date: Jun. 10, 2021

(87) PCT Pub. No.: WO2020/127487
PCT Pub. Date: Jun. 25, 2020

(65) Prior Publication Data
US 2022/0064613 A1    Mar. 3, 2022

(30) Foreign Application Priority Data
Dec. 21, 2018   (EP) .................................... 18215341

(51) Int. Cl.
*C12N 9/22* (2006.01)
*A61P 35/02* (2006.01)
(Continued)

(52) U.S. Cl.
CPC ................ *C12N 9/22* (2013.01); *A61P 35/02* (2018.01); *C12N 15/11* (2013.01); *C12N 15/907* (2013.01); *A61K 48/00* (2013.01); *C12N 2310/20* (2017.05)

(58) Field of Classification Search
CPC ........ C12N 9/22; C12N 15/11; C12N 15/907; C12N 2310/20; A61P 35/02; A61K 48/00
See application file for complete search history.

(56) References Cited

U.S. PATENT DOCUMENTS

2021/0348161 A1    11/2021   Rodriguez Perales et al.

FOREIGN PATENT DOCUMENTS

| WO | WO 2009/063426 A2 | 5/2009 | |
| WO | WO 2009/137872 A1 | 11/2009 | |
| WO | WO-2016061073 A1 * | 4/2016 | ......... A01K 67/0275 |

OTHER PUBLICATIONS

Garcia-Tunon et al., "CRISPR-Era for switching off (Onco) Genes" in Modulating Gene Expression—Abridging the RNAi and CRISPR-Cas9 Technologies, CH2. IntechOpen (Nov. 5, 2018) p. 7-26 (Year: 2018).*

(Continued)

*Primary Examiner* — Evelyn Y Pyla
*Assistant Examiner* — Katherine R Small
(74) *Attorney, Agent, or Firm* — Knobbe, Martens, Olson & Bear, LLP

(57) ABSTRACT

The present invention relates to a composition comprising a first gRNA bound to an RNA-guided endonuclease forming a first ribonucleoprotein complex, said first gRNA comprises a first targeting sequence being complementary for a first target sequence in an intron in the 5' upstream part of a fusion gene; and a second gRNA bound to an RNA-guided endonuclease forming a second ribonucleoprotein complex, said second gRNA comprises a second targeting sequence being complementary for second target sequence in an intron in the 3' downstream part of the fusion gene. Such compositions may find use in the treatment of fusion gene related cancers.

16 Claims, 10 Drawing Sheets

Specification includes a Sequence Listing.

(51) Int. Cl.
  *C12N 15/11* (2006.01)
  *C12N 15/90* (2006.01)
  *A61K 48/00* (2006.01)

(56) References Cited

OTHER PUBLICATIONS

Annala, et al., "Fusion genes and their discovery using high throughput sequencing" Cancer Lett. (2013) 340(2): 1-21 (Year: 2013).*

Santos, et al., "Comprehensive protocols for CRISPR/Cas9-based gene editing in human pluripotent stem cells" Curr Protoc Stem Cell Biol. (2016) 38: 1-82 (Year: 2016).*

Baliou et al.: "CRISPR therapeutic tools for complex genetic disorders and cancer", International J Oncol. 2018, vol. 53, No. 2, pp. 443-468.

Daly et al.: "FGFR3-TACC3 fusion proteins act as naturally occurring drivers of tumor resistance by functionally substituting for EGFR/ERK signaling", Oncogene, Jun. 27, 2016, vol. 36, No. 4, pp. 471-481.

Egashira et al.: "Chronic sun exposure-related fusion oncogenes EGFR-PPARGC1A in cutaneous squamaous cell carcinoma", Scientific Reports, Oct. 4, 2017, vol. 7, No. 1, pp. 1-14 and Supplementary Data in 20 pages.

García-Tuñón et al.: "The CRISPR/Cas9 system efficiently reverts the tumorigenic ability of BCR/ABL in vitro and in a xenograft model of chronic myeloid leukemia", Oncotarget, Feb. 9, 2017, vol. 8, No. 16, pp. 26027-26040.

García-Tuñón et al.: "CRISPR-ERA for Switching Off (Onco) Genes", In Modulating Gene Expression—Abridging the RNAi and CRISPR-Cas9 Technologies, IntechOpen; Nov. 5, 2018, 30 pages.

Gómez-H et al.: "C14ORF39/SIX6OS1 is a constituent of the synaptonemal complex and is essential for mouse fertility", Nature Comm., Oct. 31, 2016, vol. 7, No. 1, pp. 1-16 and Supplemental Information in 21 pages.

Ho et al.: "In Vivo Genome Editing as a Therapeutic Approach", International J Mol Sciences, 2018, vol. 19, No. 9, 2721 (19 pages).

Huang et al.: "Induction of apoptosis in imatinib sensitive and resistant chronic myeloid leukemia cells by efficient disruption of bcr-abl oncogene with zinc finger nucleases", J Exper Clin Cancer Res., Mar. 20, 2018, vol. 37, No. 1, 62 (14 pages).

Liu et al.: "Systemic delivery of CRISPR/Cas9 with PEG-PLGA nanoparticles for chronic myeloid leukemia targeted therapy", Biomater Science, Apr. 23, 2018, vol. 6, No. 6, pp. 1592-1603 and Supplementary Data in 9 pages.

Oppel et al.: "Specific targeting of oncogenes using CRISPR technology", Cancer Res., Sep. 7, 2018, vol. 78, No. 19, pp. 5506-5512.

Pandey et al., "$PAX_3$-$FOXO_1$ is essential for tumour initiation and maintenance but not recurrence in a human myoblast model of rhabdomyosarcoma", J Pathol. Apr. 2017, vol. 241, No. 5, pp. 626-637.

Vanoli et al., "CRISPR-Cas9-guided oncogenic chromosomal translocations with conditional fusion protein expression in human mesenchymal cells", Proc Nat Aca Sciences, Apr. 4, 2017, vol. 114, No. 14, pp. 3696-3701 and Supporting Information in 2 pages.

Wang et al., "Genetic screens in human cells using the CRISPR/Cas9 system", Science, Jan. 3, 2014, vol. 343, No. 6166, pp. 80-84.

International Search Report and Written Opinion dated Mar. 12, 2020 for Application No. PCT/EP2019/085957 filed Dec. 18, 2019.

International Preliminary Report on Patentability dated Jun. 16, 2021 for Application No. PCT/EP2019/085957 filed Dec. 18, 2019.

* cited by examiner

SEQUENCE LISTING

```
<160> NUMBER OF SEQ ID NOS: 24

<210> SEQ ID NO 1
<211> LENGTH: 20
<212> TYPE: RNA
<213> ORGANISM: Artificial Sequence
<220> FEATURE:
<223> OTHER INFORMATION: gRNA
<220> FEATURE:
<221> NAME/KEY: modified_base
<222> LOCATION: (1)..(3)
<223> OTHER INFORMATION: 2'-O-methyl 3' phosphorothioate

<400> SEQUENCE: 1
auuccugguc aagaucagcu                                              20

<210> SEQ ID NO 2
<211> LENGTH: 20
```

```
<212> TYPE: RNA
<213> ORGANISM: Artificial Sequence
<220> FEATURE:
<223> OTHER INFORMATION: gRNA
<220> FEATURE:
<221> NAME/KEY: modified_base
<222> LOCATION: (1)..(3)
<223> OTHER INFORMATION: 2'-O-methyl 3' phosphorothioate

<400> SEQUENCE: 2 auccugguc aagaucagcu                                              20

<210> SEQ ID NO 3
<211> LENGTH: 20
<212> TYPE: RNA
<213> ORGANISM: Artificial Sequence
<220> FEATURE:
<223> OTHER INFORMATION: gRNA
<220> FEATURE:
<221> NAME/KEY: modified_base
<222> LOCATION: (1)..(3)
<223> OTHER INFORMATION: 2'-O-methyl 3' phosphorothioate

<400> SEQUENCE: 3
guucacuuga gacacuuccc                                             20

<210> SEQ ID NO 4
<211> LENGTH: 20
<212> TYPE: RNA
<213> ORGANISM: Artificial Sequence
<220> FEATURE:
<223> OTHER INFORMATION: gRNA
<220> FEATURE:
<221> NAME/KEY: modified_base
<222> LOCATION: (1)..(3)
<223> OTHER INFORMATION: 2'-O-methyl 3' phosphorothioate

<400> SEQUENCE: 4
uugcuugcua aagaucuaua                                             20

<210> SEQ ID NO 5
<211> LENGTH: 20
<212> TYPE: RNA
<213> ORGANISM: Artificial Sequence
<220> FEATURE:
<223> OTHER INFORMATION: gRNA
<220> FEATURE:
<221> NAME/KEY: modified_base
<222> LOCATION: (1)..(3)
<223> OTHER INFORMATION: 2'-O-methyl 3' phosphorothioate

<400> SEQUENCE: 5
cuuuagaggc acuuuaccag                                             20

<210> SEQ ID NO 6
<211> LENGTH: 20
<212> TYPE: RNA
<213> ORGANISM: Artificial Sequence
<220> FEATURE:
<223> OTHER INFORMATION: gRNA
<220> FEATURE:
<221> NAME/KEY: modified_base
<222> LOCATION: (1)..(3)
<223> OTHER INFORMATION: 2'-O-methyl 3' phosphorothioate

<400> SEQUENCE: 6
ucuccgaccc ugcacuuagc                                             20

<210> SEQ ID NO 7
```

```
<211> LENGTH: 20
<212> TYPE: RNA
<213> ORGANISM: Artificial Sequence
<220> FEATURE:
<223> OTHER INFORMATION: gRNA
<220> FEATURE:
<221> NAME/KEY: modified_base
<222> LOCATION: (1)..(3)
<223> OTHER INFORMATION: 2'-O-methyl 3' phosphorothioate

<400> SEQUENCE: 7
gggaauucuc uaguaugaac                                                    20

<210> SEQ ID NO 8
<211> LENGTH: 20
<212> TYPE: RNA
<213> ORGANISM: Artificial Sequence
<220> FEATURE:
<223> OTHER INFORMATION: gRNA
<220> FEATURE:
<221> NAME/KEY: modified_base
<222> LOCATION: (1)..(3)
<223> OTHER INFORMATION: 2'-O-methyl 3' phosphorothioate

<400> SEQUENCE: 8
acugucagga cauagacuau                                                    20

<210> SEQ ID NO 9
<211> LENGTH: 20
<212> TYPE: RNA
<213> ORGANISM: Artificial Sequence
<220> FEATURE:
<223> OTHER INFORMATION: gRNA
<220> FEATURE:
<221> NAME/KEY: modified_base
<222> LOCATION: (1)..(3)
<223> OTHER INFORMATION: 2'-O-methyl 3' phosphorothioate

<400> SEQUENCE: 9
cacuugagau gggcccuugc                                                    20

<210> SEQ ID NO 10
<211> LENGTH: 20
<212> TYPE: RNA
<213> ORGANISM: Artificial Sequence
<220> FEATURE:
<223> OTHER INFORMATION: gRNA
<220> FEATURE:
<221> NAME/KEY: modified_base
<222> LOCATION: (1)..(3)
<223> OTHER INFORMATION: 2'-O-methyl 3' phosphorothioate

<400> SEQUENCE: 10
gagaaucuaa accugcaugc                                                    20

<210> SEQ ID NO 11
<211> LENGTH: 20
<212> TYPE: RNA
<213> ORGANISM: Artificial Sequence
<220> FEATURE:
<223> OTHER INFORMATION: gRNA
<220> FEATURE:
<221> NAME/KEY: modified_base
<222> LOCATION: (1)..(3)
<223> OTHER INFORMATION: 2'-O-methyl 3' phosphorothioate

<400> SEQUENCE: 11
cuguucugac ucuccgaggg                                                    20
```

```
<210> SEQ ID NO 12
<211> LENGTH: 20
<212> TYPE: RNA
<213> ORGANISM: Artificial Sequence
<220> FEATURE:
<223> OTHER INFORMATION: gRNA
<220> FEATURE:
<221> NAME/KEY: modified_base
<222> LOCATION: (1)..(3)
<223> OTHER INFORMATION: 2'-O-methyl 3' phosphorothioate

<400> SEQUENCE: 12
ucugcauugg uggcucuaga                                                      20

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
ctttaggtca tgcttttcag ag                                                   22

<210> SEQ ID NO 14
<211> LENGTH: 23
<212> TYPE: DNA
<213> ORGANISM: Artificial Sequence
<220> FEATURE:
<223> OTHER INFORMATION: Primer

<400> SEQUENCE: 14
ctttgatacc tcctactcat cgc                                                  23

<210> SEQ ID NO 15
<211> LENGTH: 22
<212> TYPE: DNA
<213> ORGANISM: Artificial Sequence
<220> FEATURE:
<223> OTHER INFORMATION: Primer

<400> SEQUENCE: 15
ctgtcactca aggaatgttg ac                                                   22

<210> SEQ ID NO 16
<211> LENGTH: 22
<212> TYPE: DNA
<213> ORGANISM: Artificial Sequence
<220> FEATURE:
<223> OTHER INFORMATION: Primer

<400> SEQUENCE: 16
ccttccatat ttccagacaa tg                                                   22

<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17
gccagtggag taaacagcac t                                                    21

<210> SEQ ID NO 18
<211> LENGTH: 22
<212> TYPE: DNA
```

```
<213> ORGANISM: Artificial Sequence
<220> FEATURE:
<223> OTHER INFORMATION: Primer

<400> SEQUENCE: 18
ctgagaagtt tggcaatgag ct                                              22

<210> SEQ ID NO 19
<211> LENGTH: 22
<212> TYPE: DNA
<213> ORGANISM: Artificial Sequence
<220> FEATURE:
<223> OTHER INFORMATION: Primer

<400> SEQUENCE: 19
agacactcct ctcacaggac ta                                              22

<210> SEQ ID NO 20
<211> LENGTH: 22
<212> TYPE: DNA
<213> ORGANISM: Artificial Sequence
<220> FEATURE:
<223> OTHER INFORMATION: Primer

<400> SEQUENCE: 20
ttcaactccc aagttcatgc ac                                              22

<210> SEQ ID NO 21
<211> LENGTH: 21
<212> TYPE: DNA
<213> ORGANISM: Artificial Sequence
<220> FEATURE:
<223> OTHER INFORMATION: Primer

<400> SEQUENCE: 21
gaaggcagga ataacctagt c                                               21

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
ccaagcagaa gtacgatgat aa                                              22

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
agatggcagg agtgaggagt                                                 20

<210> SEQ ID NO 24
<211> LENGTH: 20
<212> TYPE: DNA
<213> ORGANISM: Artificial Sequence
```

```
<220> FEATURE:
<223> OTHER INFORMATION: Primer

<400> SEQUENCE: 24
gtcctgtctg tctgctggaa                                              20
```

CRISPR GENE THERAPY OF FUSION GENE RELATED CANCERS

CROSS REFERENCE TO RELATED APPLICATIONS

This application is a U.S. National Phase Application of PCT International Application Number PCT/EP2019/085957, filed on Dec. 18, 2019, designating the United States of America and published in the English language, which is an International Application of and claims the benefit of priority to European Patent Application No. 18215341.1, filed on Dec. 21, 2018. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 37 U.S.C. § 1.52 (e). The name of the ASCII text file for the Sequence Listing is SeqList-PLOUG23-026APC.txt, the date of creation of the ASCII text file is Jun. 9, 2021, and the size of the ASCII text file is 6 KB.

TECHNICAL FIELD OF THE INVENTION

The present invention relates to gene therapy of fusion gene related cancers. In particular, the present invention relates to CRISPR gene therapy of fusion gene related cancers such as an AML (RUNX1)-ETO (RUNX1T1) related cancer.

BACKGROUND OF THE INVENTION

A fusion gene is a hybrid gene generated by two previously separated genes. Fusion genes are important cancer oncogenes and can be generated through translocation, interstitial deletion, or chromosomal inversion. Oncogenic fusion genes are frequent causative agents in Acute Myeloid Leukemia (AML) with more than 300 fusion genes identified so far. AML remains a major challenge to researchers and clinicians alike, despite great advances in our basic knowledge and therapeutic options. Thus, relapse is still seen in a major part (up to 80%) of patients obtaining a complete remission. Oncogenic fusions have also become increasingly important in non-small cell lung cancer.

CRISPR-Cas9 is a programmable RNA-guided gene editing tool. This system is based on a small guide RNA and the Cas9 nuclease, which can introduce specific DNA double-stranded breaks to any predesigned locus in the genome.

WO 2009/137872 discloses compositions and methods for the treatment of cancer, and is predicated at least in part on the use of gene fusion regions as therapeutic targets. The fusion region target may be physically embodied at the level of DNA, RNA or protein.

WO 2009/063426 discloses that siRNA is able to modulate hematopoietic differentiation or to inhibit the expression of a fusion product deriving from a chromosomic translocation associated to leukemia.

Hence, an improved method for treating cancer would be advantageous, and in particular a more efficient and/or reliable method for treating cancers involving fusion genes would be advantageous.

SUMMARY OF THE INVENTION

The present invention is based on the realization that the RNA-guided endonucleases (Cas9) can be used to cut out fusion (onco) gene (or parts hereof) in cancer cells. The strategy is based on a transient presence of Cas9 and the RNA guides, thus eliminating long-term off-target effects.

Advantages of the concept of the present invention are:

Not considered harmful to normal cells. This is because fusion genes are mutations where genes usually not placed in close proximity to each other are fused. This means that in normal cells (that do not contain the fusion gene) the cut sites are placed at great distance to each other- and often even on separate chromosomes. As the guides target introns, normal cells will experience a very limited number of cuts in distantly located introns. Such cuts are easy for the cell to repair and as the cut-sites are placed in introns very unlikely to lead to change in gene-product function or expression. This is exemplified in example 2 where cells that do not harbour the fusion-oncogene are unharmed by the treatment.

The method can be used without knowing the exact fusion site. Fusion sites in fusion oncogenes may appear at different location within the same intron. However, since the gRNA's can be located e.g. at the ends of the intron harbouring the fusion site or in neighbouring introns, it is not important to know the exact fusion site. This means that the same treatment (composition) can be used for large groups of patients with the same fusion-oncogenes (but different fusion sites).

The invention relies on transfer of Cas9 protein and NOT through retro-viral overexpression of Cas9 or of the targeting guides. This means that shortly after treatment the transferred Cas9 and the targeting guides are degraded by the cells-only the effect on introns remains. This is highly advantageous compared to non-transient systems as long-term effects of expressing Cas9 and/or the targeting guides may result in damaging and possibly cancer-inducing off-target effects.

Out-of-frame mutations or premature stop codons may be introduced. By carefully selecting which part of the fusion gene is to be removed cleavage sites can be selected resulting on out of frame truncated fusion genes, which will abolish normal function of the oncogene.

Example 1 shows a schematic overview of how the compositions of the inventions can be implemented. Examples 2-4 show that the method efficiently functions in a leukemia cell line harboring the AML-ETO fusion oncogene. Example 5 shows that the method also functions in two different non-small cell lung carcinoma cell lines harboring the EML4-ALK fusion oncogene and the SLC34A2-ROS1 fusion oncogene respectively. Example 6 shows that the method functions in primary patient derived cancer cells. Example 7 shows that the method functions in a mice xenograft model of AML. Overall, the data indicate that the concept of the invention is generally applicable to fusion oncogenes in different cancer types.

Thus, an object of the present invention relates to the provision of improved treatment of diseases involving acquired fusion genes.

In particular, it is an object of the present invention to provide improved treatment of cancers comprising fusion oncogenes.

Thus, one aspect of the invention relates to a composition (for removing/destroying/redesigning acquired gene modifying oncogenes) comprising a first gRNA bound to an RNA-guided endonuclease forming a first ribonucleoprotein complex, said first gRNA comprises a first targeting sequence being complementary for a first target sequence in an intron in the 5' upstream part of a fusion gene; and a second gRNA bound to an RNA-guided endonuclease forming a second ribonucleoprotein complex, said second gRNA comprises a second targeting sequence being complementary for second target sequence in an intron in the 3' downstream part of the fusion gene.

Another aspect of the present invention relates to the composition according to the invention, for use as a medicament.

Yet another aspect of the present invention is to provide the composition according to the invention, for use in the treatment or alleviation of a cancer, preferably wherein said cancer genotype comprises a cancer inducing fusion gene (fusion oncogene).

Still another aspect of the present invention is to provide an in vitro method for deleting part of a fusion gene in a cell, the method comprising incubating the cell with a composition according to the invention.

A further aspect relates to a kit of parts comprising

A first vial comprising a first gRNA bound to an RNA-guided endonuclease forming a first ribonucleoprotein complex, said first gRNA comprises a first targeting sequence being complementary for a first target sequence in an intron in the 5' upstream part of a fusion gene;

A second vial comprising a second gRNA bound to an RNA-guided endonuclease forming a second ribonucleoprotein complex, said second gRNA comprises a second targeting sequence being complementary for second target sequence in an intron in the 3' downstream part of the fusion gene;

optionally, one or more further vials comprising one or more further gRNA's bound to an RNA-guided endonuclease forming further ribonucleoprotein complexes, said further gRNA's comprising further targeting sequences being complementary for further target sequences in an intron in the 5' upstream part of the fusion gene or a further target sequence in an intron in the 3' downstream part of the fusion gene; and optionally, instructions for using the kit to delete part of the fusion gene by the gRNAs bound to the RNA-guided endonuclease in a cell or a subject.

Figure 1:
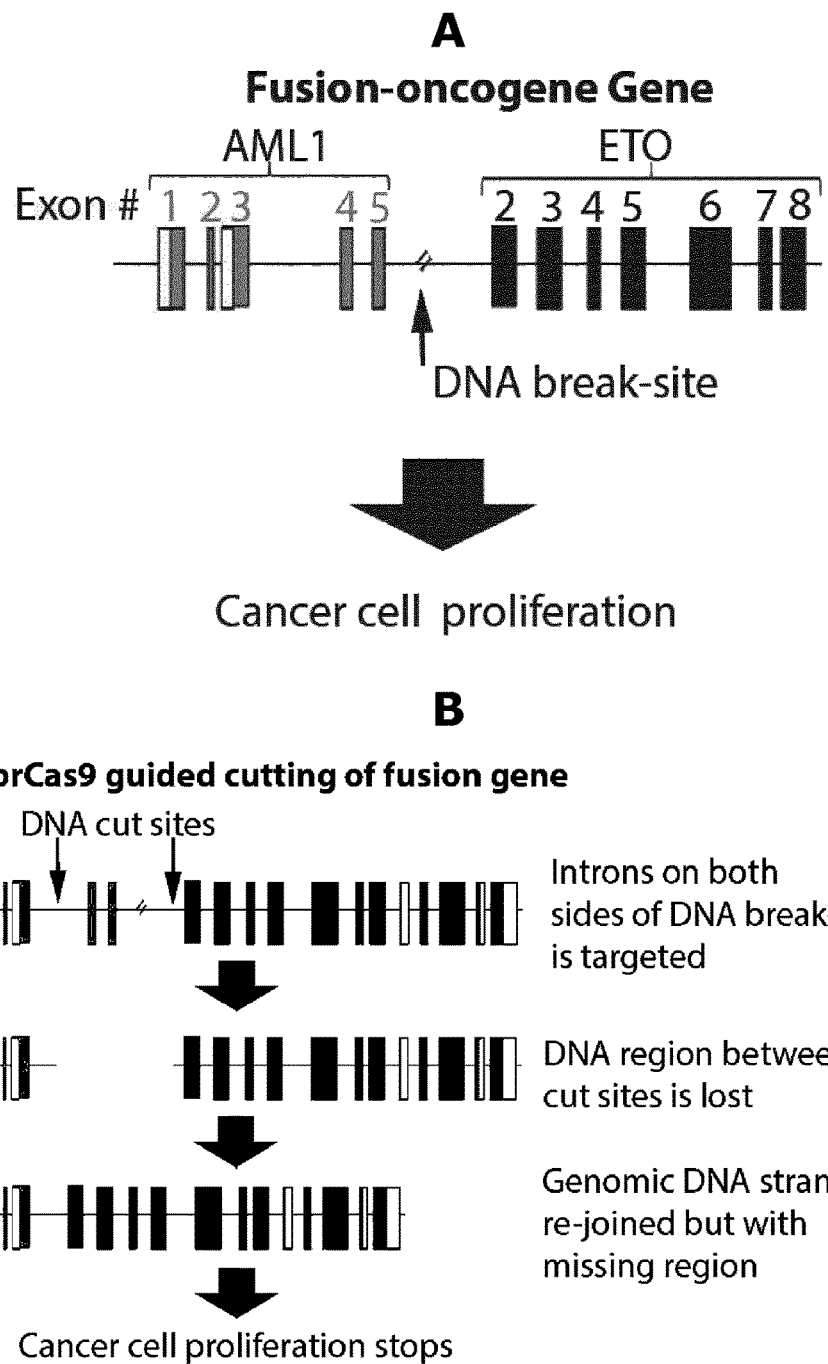
FIG. 1 shows the principle of the invention exemplified by Acute Myeloid Leukemia (AML). A) Schematic representation of the AML1-ETO fusion gene. AML is a type of cancer often driven by oncogenic fusion genes. Exons from each gene is indicated by numbers. Exons are presented by boxes. Introns are indicated by lines between boxes (exons). The fusion site (DNA break site) is indicated by "\\". B) Shows the principle behind the present invention. Top: binding sites for the gRNAs are indicated by arrows. gRNA's bind on each side of the fusion site. Middle: Upon cleavage of the oncogene by the composition of the invention a part of the fusion gene is deleted. Bottom: After in vivo repair, a new non-functional oncogene is produced. The gRNA's can be preferably be positioned to induce a frameshift or a premature stop codon.

The present invention will now be described in more detail in the following.

DETAILED DESCRIPTION OF THE INVENTION

Definitions

Prior to discussing the present invention in further details, the following terms and conventions will first be defined:

Oncogene

In the present context, the term "oncogene" refers to a gene that has the potential to cause cancer.

Fusion Gene

In the present context, a "fusion gene" is a hybrid gene formed from two previously separate genes. It can e.g. occur as a result of: translocation, interstitial deletion, or chromosomal inversion. Fusion genes can contribute to tumour formation because fusion genes can produce much more active abnormal protein than non-fusion genes. Often, fusion genes are oncogenes that cause cancers. Oncogenic fusion genes may lead to a gene product with a new or different function from the two fusion partners. Non-limiting examples include BCR-ABL, TEL-AML1, AML1-ETO, and TMPRSS2-ERG.

Since chromosomal translocations play such a significant role in neoplasia, a specialized database of chromosomal aberrations and gene fusions in cancer has been created. This database is called Mitelman Database of Chromosome Aberrations and Gene Fusions in Cancer.

CRISPR/Cas9

CRISPR/Cas9, is an RNA-guided targeted genome editing tool allowing e.g. for gene knockout, knock-in SNPs, insertions and deletions in cell lines and animals. The CRISPR/Cas9 genome editing system requires two components, Cas9, the RNA-guided endonuclease, and a guide RNA (gRNA); the gRNA guides Cas9 to the location in the genome sequence specifically. With the protospacer-adjacent motif (PAM—the sequence NGG for SpCas9) present at the 3' end, Cas9 will unwind the DNA duplex and cleave both strands upon recognition of a target sequence by the guide RNA. Cas9 is the most widely used RNA-guided endonuclease but other RNA-guided endonucleases exist.

sgRNA

Synthetic single guide RNA has been recognized as the preferred way for highly efficient and accurate editing. The synthetic single gRNA may be a pure 100-mer RNA oligo that contains the targeting gRNA sequence and the tracrRNA scaffold in a single entity.

Compositions

As outlined above, the present invention is based on the realization that the RNA-guided endonucleases can be used to cut out a fusion (onco) gene (or parts hereof) in cancer cells. The strategy is based on a transient presence, thus eliminating long-term off-target effects. Thus, an aspect of the invention relates to a composition (for removing and/or destroying and/or redesigning acquired gene modifying oncogenes) comprising a first gRNA bound to an RNA-guided endonuclease forming a first ribonucleoprotein complex, said first gRNA comprises a first targeting sequence being complementary for a first target sequence in an intron in the 5' upstream part of a fusion gene; and a second gRNA bound to an RNA-guided endonuclease forming a second ribonucleoprotein complex, said second gRNA comprises a second targeting sequence being complementary for second target sequence in an intron in the 3' downstream part of the fusion gene.

As also outlined above, example 1 shows a schematic overview of how the compositions of the inventions can be implemented. Examples 2-4 show that the method efficiently functions in a leukemia cell line harbouring the AML-ETO fusion oncogene. Example 5 shows that the method also functions in two different non-small cell lung carcinoma cell lines harbouring the EML4-ALK fusion oncogene and the SLC34A2-ROS1 fusion oncogene respectively. The EML4-ALK fusions are generated through inversion on chromosome 2, whereas the SLC34A2-ROS1 fusion is generated through a translocation as is also the AML-ETO fusion. Thus, the data overall indicate that the concept of the invention is generally applicable to fusion oncogenes generated through different molecular mechanisms and in different cancer types.

As outlined above, the composition is particularly relevant for removing a part of a fusion oncogene. Thus, in a preferred embodiment the fusion gene is an oncogene.

Certain genes are more often involved in fusion oncogenes than others. Thus, in an embodiment, the fusion gene comprises a gene sequence selected from the group consisting of ALK, ROS1, RET, CIC, ERG, BRAF, EGFR, HER2, TERT, FGFR1, FGFR2, FGFR3, NTRK1, NTRK2, NTRK3, BCOR, FGR, MET, PDGFRA, PDGFRB, PIK3CA, SSX1, SSX2, SSX4, EWSR1, FUS, PDGFB, ETV1, PAX3, PAX7, PAX8, KMT2A, ABL1, RUNX1, RARA, and TCF3. The above fusion gene partners are often seen in solid tumours.

The upstream part (5'-end) of fusion oncogenes may be constituted of parts of different genes. Certain genes however, are more often seen as the upstream part (5'-end) of fusion oncogenes. Thus, in another embodiment, the upstream part of the fusion gene comprises a gene sequence selected from the group consisting of AML1, SLC34A2, EML4, CIC, EWSR1, HER2, BCOR, KMT2A, FUS, PAX3, PAX7, PAX8, FGFR1, FGFR2 and FGFR3.

Similar, the downstream part (3'-end) of fusion oncogenes may be constituted of parts of different genes. Certain genes however, are more often seen as the downstream part (3'-end) of fusion oncogenes. Thus, in yet another embodiment, the downstream part of the fusion gene comprises a gene sequence selected from the group consisting of ETO, AML1, ALK, RET, ROS1, ABL1, ERG, BRAF, HER2, NTRK1, NTRK2, NTRK3, SSX1, SSX2, SSX4, FGFR1, FGFR2, FGFR3, PDGFRA, PDGFRB, EGFR, and MET.

In yet an embodiment the fusion gene is selected from the group consisting of ETV6-AML1, TCF3-PBX1 CBFB-MYH11, PML-RARA, BCR-ABL1, GTF2I-RARA, VAV1-GSS, ITK-FER, IKZF-ERBB4, NPM-ALK, and AF4-MLL. ETV6-AML1 and TCF3-PBX1 are seen in ALL, CBFB-MYH11 is often seen in AML, PML-RARA and GTF2I-RARA is often involved in APL, BCR-ABL1 is seen in CML and ALL, VAV1-GSS, ITK-FER and IKZF-ERBB4 are seen in PTCL.

In yet another embodiment, the fusion gene is selected from the group consisting of EML4-ALK, BCR-ABL1, CCDC6-RET, TMPRSS2-ERG, NCOA4-RET, KIF5B-RET, TCF3-PBX1, KMT2A-AFF1, KIF5B-ALK, ETV6-RUNX1, EWSR1-FLI1, STIL-TAL1, CD74-ROS1, EWSR1-ERG, RUNX1-RUNX1T1, KIAA1549-BRAF, PAX8-PPARG, SLC34A2-ROS1, NPM1-ALK, SS18-SSX2, SS18-SSX1, PAX3-FOXO1, PRKAR1A-RET, EZR-ROS1, TMPRSS2-ETV1, ETV6-NTRK3, PAX7-FOXO1, CD74-NRG1, NUP214-ABL1, PML-RARA, ETV6-ABL1, YWHAE-NUTM2B, YWHAE-FAM22A, SDC4-ROS1, LRIG3-ROS1, KMT2A-MLLT1, CRTC1-MAML2, TPM3-NTRK1, FUS-DDIT3, CBFA2T3-GLIS2, STRN-ALK, TFG-NTRK1, SET-NUP214, TMPRSS2-ETV4, COL1A1-PDGFB, KMT2A-MLLT3, TPM3-ROS1, EWSR1-ATF1, EWSR1-DDIT3, TFG-ALK FUS-CREB3L2, FGFR3-TACC3, CRTC3-MAML2, HMGA2-LPP, KLC1-ALK, NAB2-STAT6, AKAP9-BRAF, TBL1XR1-TP63, GOLGA5-RET, EWSR1-WT1, SLC45A3-ERG, SS18-SSX4, GOPC-ROS1, FUS-CREB3L1, TPM3-ALK, ASPSCR1-TFE3, HNRNPA2B1-ETV1, SLC45A3-ETV1, ERC1-RET, ETV6-JAK2, DNAJB1-PRKACA, EWSR1-NR4A3, HER2-TMEM98, HER2-GRB7, MDK-HER2, NOS2-HER2, ZNF207-HER2, BCOR-CCNB3, BCOR-MAML3, FIP1L1-PDGFRA, ETV6-PDGFRB, CCDC6-PDGFRB, KIAA1509-PDGFRB, CIC-DUX4, CIC- DUX4L10, CIC-FOXO4, TRIO-TERT, BCR-PDGFRA, BRD4-NUTM1 and CLTC-ALK. Thus, many cancer-related fusion oncogenes have been identified.

Some fusion oncogenes are considered especially relevant to treat e.g. due to their severity or abundance. Thus, in a preferred embodiment, the fusion oncogene is selected from the group consisting of AML1-ETO, ETV6-AML1, BCR-ABL1, SLC34A2-ROS1, CD74-ROS1, KIF5B-ALK, EML4-ALK, CCDC6-RET, KIF5B-RET, NCOA4-RET, EWSR1-ERG, EWSR1-FLI, ETV6-NTRK3, TMP3-NTRK1, and SS18-SSX1, SS18-SSX2.

The exact position on the target sequence in the upstream part of the fusion gene may vary. Thus, in an embodiment, the first target sequence for the first ribonucleoprotein complex is positioned in one of the five introns closest to the fusion site, in the 5' upstream part of a fusion gene, such as in one of the four introns closest to the fusion site, preferably such as in one of the three introns closest to the fusion site, more preferably in one of the two introns most closest to the fusion site, even more preferably in the second intron closest to the fusion site. It is to be understood that if the fusion site is in an intron (which is often the case), the intron closest to the fusion site is the intron harbouring the fusion site.

Similarly, the exact position on the target sequence in the downstream part of the fusion gene may vary. Thus, in yet an embodiment, the second target sequence for the second ribonucleoprotein complex, is positioned in one of the five introns closest to the fusion site, in the 3' downstream part of a fusion gene, such as in one of the four introns closest to the fusion site, preferably such as in one of the three introns closest to the fusion site, more preferably in one of the two introns most closest to the fusion site, even more preferably in the second intron closest to the fusion site. Again, it is to be understood that if the fusion site is in an intron (which is often the case), the intron closest to the fusion site is the intron harbouring the fusion site). Without being bound by theory, it is believed that it may be an advantage to cleave out the first exon of the downstream part of the fusion gene, since the oncogenic effect is often localized to the downstream part. Even more preferably, the oligonucleotides are designed to remove a section of the fusion gene which (after repair) will result in a frameshift or a premature stop codon. In the example section, the guides were designed to induce a frameshift after cleavage and repair. Thus, in a preferred embodiment, the target sequence for the first ribonucleoprotein complex is positioned in one of the three introns closest to the fusion site, in the 5' upstream part of a fusion gene (site), more preferably in one the two introns closest to the fusion site, and even more preferably in the intron second closest to the fusion site; and the target sequence for the second ribonucleoprotein complex is positioned in one of the three introns closest to the fusion site, (in the 3' downstream part of a fusion site) more preferably in one the two introns closest to the fusion site, and even more preferably in the intron second closest to the fusion site.

It is also believed that by having the cleavage sites positioned as close to each other as possible, will improve the chance that the desired fusion gene will be produced.

The exact length of the targeting sequences in the gRNA's may vary. Thus, in an embodiment, the first targeting sequence of the first ribonucleotide has a length of 17-24 nucleotides, such as 18-22, preferably 19-21, and even more preferably 20 nucleotides. In a related embodiment, the second targeting sequence of the second ribonucleotide has a length of 17-24 nucleotides, such as 18-22, preferably 19-21, and even more preferably 20 nucleotides. It is to be understood that in the present context the term "targeting sequence" relates to the part of the gRNA's, which is complementary to a "target site" in the fusion gene.

Different types of gRNA's may be used. Thus, in yet an embodiment, the gRNA is an sgRNA comprising the targeting gRNA sequence and the tracrRNA scaffold in a single entity. In yet an embodiment, the length of the sgRNA's is in the range 90-120 nt, such as 90-110 nt, preferably such as 95-105 nt, even more preferably 100 nt.

In an embodiment, the genomic target sequence is positioned 5' or 3' to a PAM motif (protospacer adjacent motif). Depending on the type of RNA guided endonuclease the PAM motif may be located either 5' or 3' to the genomic target sequence.

In an embodiment, the RNA guided endonuclease cleaves double-stranded DNA (induce double strand breaks). In yet an embodiment, the RNA guided endonuclease is selected from group consisting of Cas9 endonucleases, including SpCas9, SaCas9, NmCas9, StCas9, Cas-X, CasY, and other forms of Cas9 orthologs, CRISPR-Cpf1 endonuclease and other form of programmable DNA endonucleases, including ZFNs and TALENS.

As also outlined above, different sets of gRNA's should be designed for each specific fusion gene to be targeted. Thus, in an embodiment, said first gRNA comprises a targeting sequence selected from the group consisting of SEQ ID NO: 1-2, 5-6, 9-10 and said second gRNA comprises a targeting sequence selected from the group consisting of SEQ ID NO: 3-4, 7-8 and 11-12. As apparent from table 1, different sets may be combined depending on the specific fusion oncogene to target. Similar more than 1 gRNA may be used for each part of the fusion gene.

TABLE 1 gRNA sequences

| SEQ ID | Name | Sequence | Target |
|---|---|---|---|
| 1 | AML1 gRNA 2 | 5'AUUCCUGGUCAAGAUCAGCU...scaffold...UUU-3' | AML |
| 2 | AML1 gRNA 3 | 5'AUGCACUCCCCUCAAUUCAG...scaffold...UUU-3' | AML |
| 3 | ETO gRNA2 | 5'GUUCACUUGAGACACUUCCC...scaffold...UUU-3' | ETO |

TABLE 1-continued gRNA sequences

| SEQ ID | Name | Sequence | Target |
|---|---|---|---|
| 4 | ETO gRNA3 | 5'UUGCUUGCUAAAGAUCUAUA...scaffold...UUU-3' | ETO |
| 5 | SLC34A2 gRNA 1 | 5'CUUUAGAGGCACUUUACCAG...scaffold...UUU-3' | SLC34A2 |
| 6 | SLC34A2 gRNA 2 | 5'UCUCCGACCCUGCACUUAGC...scaffold...UUU-3' | SLC34A2 |
| 7 | ROS1 gRNA 1 | 5'GGGAAUUCUCUAGUAUGAAC...scaffold...UUU-3' | ROS1 |
| 8 | ROS1 gRNA 2 | 5'ACUGUCAGGACAUAGACUAU...scaffold...UUU-3' | ROS1 |
| 9 | EML4 gRNA 1 | 5'CACUUGAGAUGGGCCCUUGC...scaffold...UUU-3' | EML4 |
| 10 | EML4 gRNA 2 | 5'GAGAAUCUAAACCUGCAUGC...scaffold...UUU-3' | EML4 |
| 11 | ALK gRNA 1 | 5'CUGUUCUGACUCUCCGAGGG...scaffold...UUU-3' | ALK |
| 12 | ALK gRNA 2 | 5'UCUGCAUUGGUGGCUCUAGA...scaffold...UUU-3' | ALK |

Bold: 2'-O-methyl 3' phosphorothioate (the first three 5' and 3' terminal RNA residues). Underlining: tracrRNA scaffold (See e.g. Nat Biotechnol. 2015 September; 33 (9): 985-989). TracrRNA=80 nt.

The guides presented in table 1 are the ones tested in the example section. As outlined above different guides can be designed for different fusion genes.

To improve the cleavage efficiency two or more target sequences may be targeted on each site of the fusion site. Thus, in an embodiment, the composition further comprises one or more further gRNA's bound to an RNA guided endonuclease forming further ribonucleoproteins complexes, said further gRNA's comprises a further targeting sequence being complementary for a further target sequence in an intron in the 5' upstream part of a fusion gene and/or a further target sequence in an intron in the 3' downstream part of the fusion gene. In example 2, it is verified that the method works when both one and two sequences are targeted on each site of the fusion site.

In a related embodiment, the composition comprises in the range 1-8 further gRNA's bound to an RNA guided endonuclease, preferably in the range 1-4 further gRNA's bound to an RNA guided endonuclease, such as 1-4, such as 1-3, such as 1-2 or such as 2.

To increase hybridization efficiency and/or avoid degradation, the gRNA's may be modified. Thus, in yet an embodiment, the gRNA comprises artificial nucleotides, such as Bridged nucleic acids (BNAs), Locked nucleic acids (LNA) and 2-Methyl-RNA (see e.g. Nature Communications. volume 9, Article number: 1448 (2018)). In the example section gRNA's have been used which comprises three 2-Methyl-RNA's at each end. Thus, in yet an embodiment, the artificial nucleotides are positioned in one or more of position 1-5 in the 5'-end and/or 3'-end of the gRNA, preferably in position 1-5 of both the 5'-end and/or 3'-end of the gRNA, such as position 1-4 of both the 5'-end and/or 3'-end of the gRNA, such as position 1-3 of both the 5'-end and/or 3'-end of the gRNA, such as position 1-2 of both the 5'-end and/or 3'-end of the gRNA, such as position 1 of both the 5'-end and/or 3'-end of the gRNA.

To improve delivery of the ribonucleoprotein complexes of the invention, these complexes (alone or in combination) may be formulated into delivery vehicles, which improve in vivo delivery efficiency. Thus, in an embodiment, the ribonucleoprotein complexes are present, alone or in combination in a delivery vehicle. Thus, each ribonucleoprotein complex may be in its own vehicle, or different complexes may be in the same vehicle. The strategy depends on the vehicle selected. Different delivery vehicles are described Lino et al. Drug Deliv. 2018 November; 25 (1): 1234-1257.

Different types of delivery vehicles exist, which are known to the skilled person in the field. Thus, in an embodiment, the vehicle is selected from the group consisting of nanoparticle formulations, such as polymer based nanoformulations, metal-based nanoparticle formulations, gold nanoparticle formulation, graphite nanoparticle formulation and nanocapsule formulations. Preferably, the nanoparticle is a gold nanoparticle formulation, such as colloidal gold nanoparticles (Shahbazi et al. Nature Materials volume 18, pages 1124-1132 (2019) and WO2018226762 (A1)).

In another embodiment, the vehicle is selected from the group consisting of lipid-based formulations, such as cationic lipid-based formulations.

In yet an embodiment, the vehicle is selected from the group consisting of virus particle carriers, such as adeno associated virus particles, adeno associated virus derived particles, lentivirus particles, and lentivirus derived particles. In yet a further embodiment, vehicle is selected from the group consisting of nucleotide-based scaffold formulations, such as scaffold formulations containing DNA and scaffold formulations containing RNA.

Medicaments

As outlined above, the compositions of the invention is particular suited for treatment of cancers involving fusion oncogenes. Thus, an aspect of the invention relates to the composition according to the invention for use as a medicament.

In yet an aspect, the invention relates to the composition according to the invention for use in the treatment or alleviation of a cancer, preferably wherein said cancer genotype comprises a cancer inducing fusion gene (fusion oncogene).

In an embodiment, said fusion gene is selected from the group consisting of AML1-ETO, ETV6-AML1, BCR-ABL1, SLC34A2-ROS1, CD74-ROS1, KIF5B-ALK, EML4-ALK, CCDC6-RET, KIF5B-RET, NCOA4-RET, EWSR1-ERG, EWSR1-FLI, ETV6-NTRK3, TMP3-NTRK1, SS18-SSX1, and SS18-SSX2.

In another embodiment, said cancer is leukemia, such as ALL, AML, APL, CML, and lymphoma, such as PTCL, ALCL, and DLBCL.

In another embodiment, said cancer is selected from the group consisting of solid cancers, such as selected from the group consisting of lung cancer, sarcoma, glioma, thyroid cancer, melanoma, urothelial cancer, colorectal cancer, breast cancer and lymphoma.

Yet an aspect of the invention relates to a method for treating or ameliorating a subject suffering from a fusion gene related cancer, the method comprising administrating to the subject a composition according to the invention.

In an embodiment, the treatment or amelioration is caused by a partial deletion of the fusion gene by the gRNAs bound to the endonucleases.

In another embodiment, the partial fusion gene deletion by the gRNAs bound to the RNA-guided endonuclease, results in an out-of-frame protein or a premature stop codon in the remaining fusion gene (causing incomplete translation into the potential onco-protein).

Yet an aspect of the invention relates the use of a composition according to the invention for the manufacture of a medicament. In an embodiment, said medicament, is for treatment or amelioration of a cancer involving a genotype comprising a cancer inducing fusion gene.

In a general embodiment, the partial fusion gene deletion by the gRNAs bound to the RNA-guided endonuclease, results in an out-of-frame gene product or a premature stop codon in the remaining fusion gene (causing incomplete translation into the potential onco-protein).

In another general embodiment, said subject is a mammal, preferably a human.

In Vitro

Besides finding use as medicaments, the compositions according to the invention may also be used in vitro. Thus, a further aspect of the invention relates to an (in vitro) method for deleting part of a fusion gene in a cell, the method comprising incubating the cell with a composition according the invention.

In an embodiment, the partial fusion gene deletion by the gRNAs bound to the RNA-guided endonuclease, results in an out-of-frame gene product or a premature stop codon in the remaining fusion gene (causing incomplete translation into the potential onco-protein).

In a preferred embodiment, the cell is a human cell.

Kit of Parts

The different gRNA's bound to an RNA-guided endonuclease according to the invention may not be present in the same composition before use, but may be stored in different vials/containers. Thus, yet another aspect of the invention relates to a kit of parts comprising a first vial comprising a first gRNA bound to an RNA-guided endonuclease forming a first ribonucleoprotein complex, said first gRNA comprises a first targeting sequence being complementary for a first target sequence in an intron in the 5' upstream part of a fusion gene;

a second vial comprising a second gRNA bound to an RNA-guided endonuclease forming a second ribonucleoprotein complex, said second gRNA comprises a second targeting sequence being complementary for second target sequence in an intron in the 3' downstream part of the fusion gene;

optionally, one or more further vials comprising one or more further gRNA's bound to an RNA-guided endonuclease forming further ribonucleoprotein complexes, said further gRNA's comprising further targeting sequences being complementary for further target sequences in an intron in the 5' upstream part of the fusion gene and/or a further target sequence in an intron in the 3' downstream part of the fusion gene; and optionally, instruction for using the kit to delete part of the fusion gene by the gRNAs bound to the RNA-guided endonuclease in a cell or a subject.

As also outlined above, to improve delivery of the ribonucleoprotein complexes of the invention, these complexes (alone or in combination) may be formulated into delivery vehicles, which improve in vivo delivery. Thus, in an embodiment, the ribonucleoprotein complexes are present, alone or in combination in a delivery vehicle.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples.

EXAMPLES

Example 1—Schematic Overview of Method

The present example exemplifies the concept of the invention in relation to AML. Acute Myeloid Leukemia (AML) is a type of cancer often driven by oncogenic fusion genes. One of the most common fusion-oncogenes in AML is the AML1 gene fused to the ETO1 gene creating the AML1-ETO fusion gene (FIG. 1A). The fact that the genetic codes of AML and the ETO are in close proximity to each in the cancer cells that harbour this fusion onco-gene makes it targetable by the CRISPR Cas9 guided approach according to the present invention. By designing RNA-guides (gRNA) that target introns on each side of the fusion site, vital part of the genomic code can be cut out for the fusion-oncogene (FIG. 1B), which leads to non-functional oncogenes. This will stop cancer cell proliferation.

Non-cancer cells do not have AML and ETO genes in close proximity on the genome. Thus, no vital parts of either gene will therefore not be cut out. In essence, non-cancer cells are left unharmed.

Example 2—AML-ETO Leukemia Cell Line

Aim of Study

To verify that the method of the invention can inhibit cell proliferation of cancer cells line harbouring an AML-ETO fusion gene. Further, to verify that the treatment does not affect the growth of cells that do not harbour an AML-ETO fusion gene.

Materials and Methods

Cell Maintenance:

Kasumi-1 cells and THP-1 cells were cultured at 37° C., 5% $CO_2$. Kasumi-1 cells were maintained in RPMI 1640 (Sigma) supplemented with 20% bovine growth serum (Sigma) streptomycin, penicillin, and L-glutamine (Gibco). THP-1 cells were maintained in RPMI 1640 (Sigma) supplemented with 10% bovine growth serum (Sigma), streptomycin, penicillin, and L-glutamine (Gibco).

Guide RNA's:

The target regions of the AML and ETO gRNAs were selected in order to create an out-of-frame deletion of AML1-ETO transcript leading to a premature stop codon.

The specific guides used are indicated in table 1 as SEQ ID NO's: 1-4.

Electroporation:

Both cell type was nucleofected using 4D nucleofector from Lonza-X unit (program CM 138) with opti-MEM (Gibco) as nucleofection buffer. 5 µg Cas9 nuclease V3 protein (IDT) was complexed with 2.7 µg chemically modified sgRNA (Synthego) for 15 min at RT. RNPs were made separately and pooled before nucleofection. $5×10^5$ cells were washed in PBS (Sigma) and resuspended in nucleofection buffer.

The gRNAs bound to the Cas9 endonuclease as a ribonucleoprotein (RNP) complex were electroporated into the kasumi-1 cells followed by PCR analysis to screen for the targeted deletion and validated by sequencing using primers flanking the targeted regions. RNPs were nucleofected into cells in a volume of 20 µl. Directly after nucleofection cells were incubated at 37° C., 5% CO2.

Cell Proliferation:

The rate of cell proliferation following nucleofection was assessed with 0.4% tryphan blue on a TC20 automated cell counter (Biorad). 1 day after nucleofection cells were counted and then every second day cells were counted for a week.

Results

Figure 2:
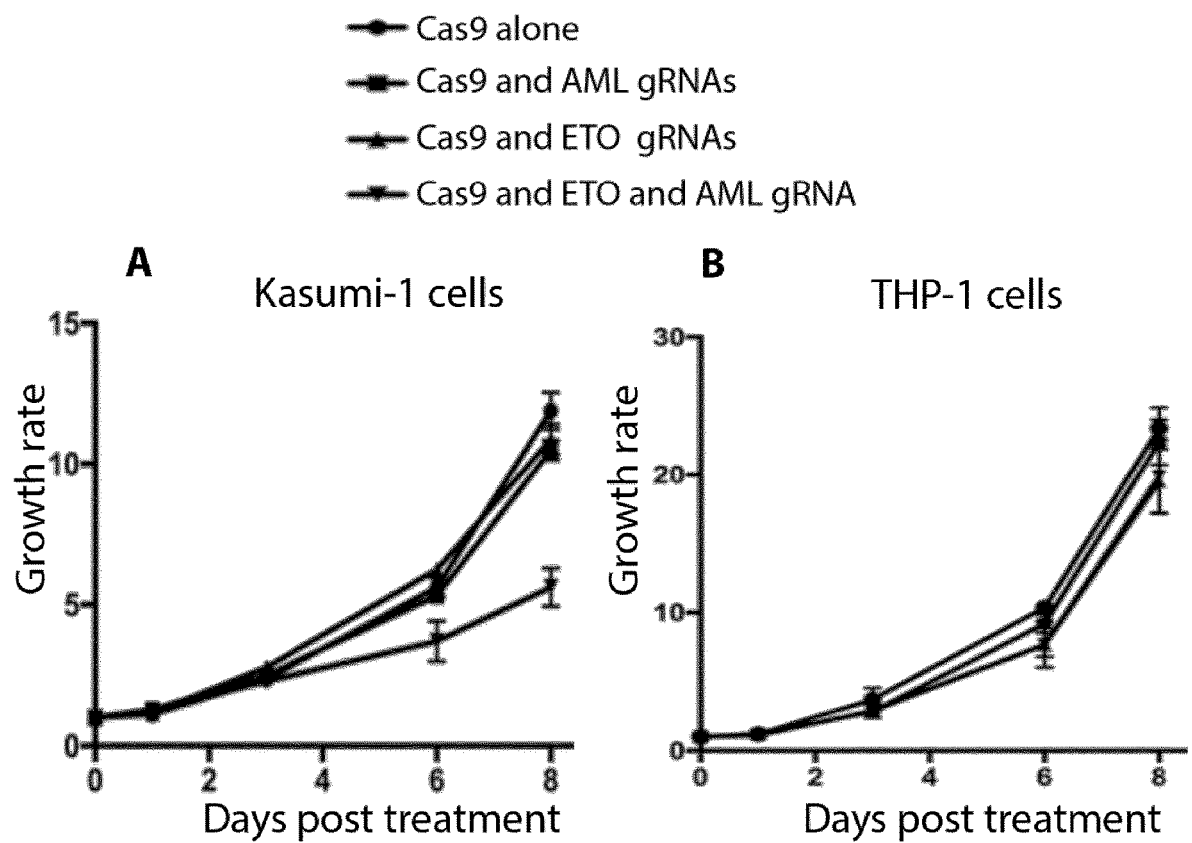
FIG. 2 shows cell growth using the method of the invention. Cells were treated with either no gRNAs (negative control), only AML gRNA's, only ETO gRNA's or AML and ETO gRNA's. A) The Kasumi cell line—an AML derived cell line that harbours the AML1-ETO fusion-oncogene. B) THP-1 cell line-AML-derived cell line that does NOT harbour the AML1-ETO fusion oncogene.

The Kasumi cell line is an AML derived cell line that harbours the AML1-ETO fusion-oncogene. Treating this cell line with Cas9 and with guides that target an intron in ETO and guides that target an intron in AML led to a significant growth retardation (FIG. 2A). Treating the cells with only ETO guides, only AML guides, or no guides did not lead to a growth retardation (FIG. 2A). Further, treating cells of another AML-derived cell line (THP-1) that does NOT harbour the AML1-ETO fusion oncogene did not lead to a growth retardation (FIG. 2B).

Thus, upon treatment with AML and ETO RNPs, cell proliferation is significantly suppressed indicating that the method is able to make a targeted deletion of the oncogenic AML-ETO protein in leukaemia cells (FIG. 2A).

Conclusion

The data indicate that the method of the invention is able to induce a targeted deletion of part of the AML-ETO oncogene. The data further clearly shows that the method is able to induce cancer cell killing without harming cells, which do not have the fusion gene.

Example 3—PCR Verification of the Method of the Invention

Aim of Study

To verify by PCR that part of the AML1-ETO fusion oncogene is indeed cut out.

Materials and Methods

Electroporation:

See example 2.

Cell Maintenance:

Kasumi-1 cells were used for this example. See example 2 for details.

Genomic DNA Extraction:

2 days after nucleofection, dead cells were removed with low centrifugation and genomic DNA was harvested using QIAamp DNA mini kit (QIAGEN) following manufactures protocol. A PCR amplicon spanning the sgRNA genomic target sites were generated using Onetaq DNA polymerase (NEB) with a pair of screening primers (table 2) and analysed on 1.5% agarose gel. PCR products were purified with gel extraction kit (QIAGEN) according to manufactures protocol and sanger-sequenced using both PCR primers.

The following primers were used:

TABLE 2

| SEQ ID | Name   | Sequence                       | Target |
|--------|--------|--------------------------------|--------|
| 13     | AML1 F | 5'-CTTTAGGTCATGCTTTTCAGAG-3'   | AML    |
| 14     | AML1 R1| 5'-CTTTGATACCTCCTACTCATCGC-3'  | AML    |
| 15     | ETO F  | 5'-CTGTCACTCAAGGAATGTTGAC-3'   | ETO    |
| 16     | ETO R  | 5'-CCTTCCATATTTCCAGACAATG-3'   | ETO    |

Results

Figure 3A:
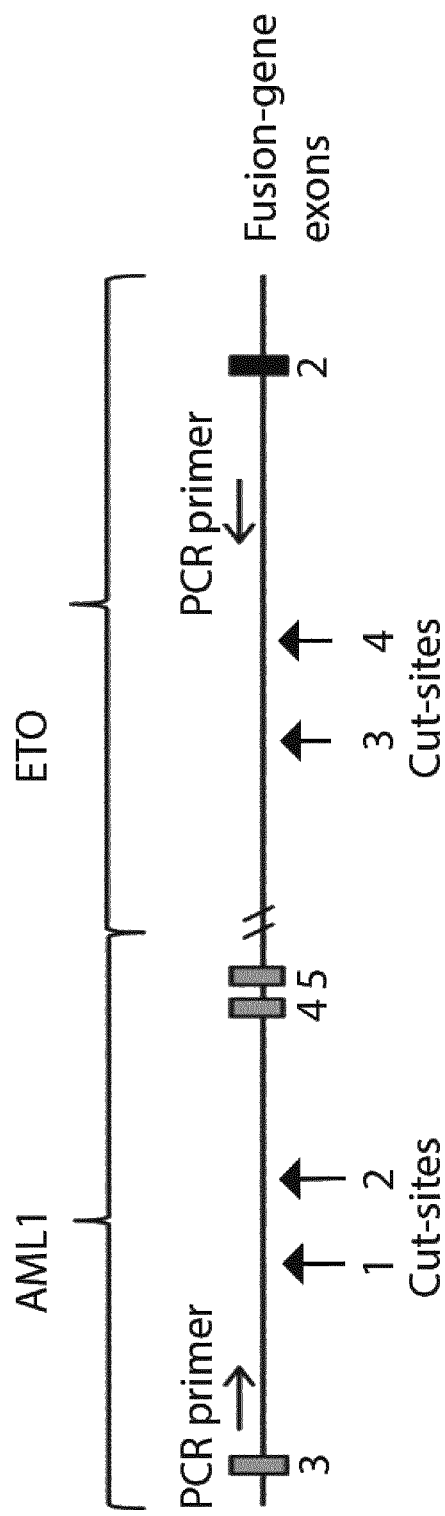
FIG. 3 shows that the deletion is detectable by PCR. Two guides targeting an AML intron (cut-sites 1 and 2) and two guides targeting an ETO intron (cut-sites 3 and 4) were used. PCR primers flanking the DNA region targeted by the guides (3A) were designed. If the RNA guides mediated cutting, PCR products of 4 different sizes could be expected, whereas "no-cutting" would lead to a PCR product too long to amplify (3B). This is exactly what was found when analyzing the PCR product from Kasumi-1 cells that were treated with the RNA guides either in combination where all guides were used and each intron therefore targeted by two guides (3B) or in setups where the guides were combined in pairs and each intron therefore was only targeted by a single guide (3C).

The gRNA's targeting an AML intron and guides targeting an ETO intron were used. In the example displayed in FIG. 3A sets of two guides (two for the AML-intron and two for the ETO-intron) were used. PCR primers placed in the flanking regions were designed (see table 2). If the cutting works, it was expected that the PCR primers would give rise to four PCR products of different lengths depending on how the guides cut the genomic DNA.

Figure 3B:
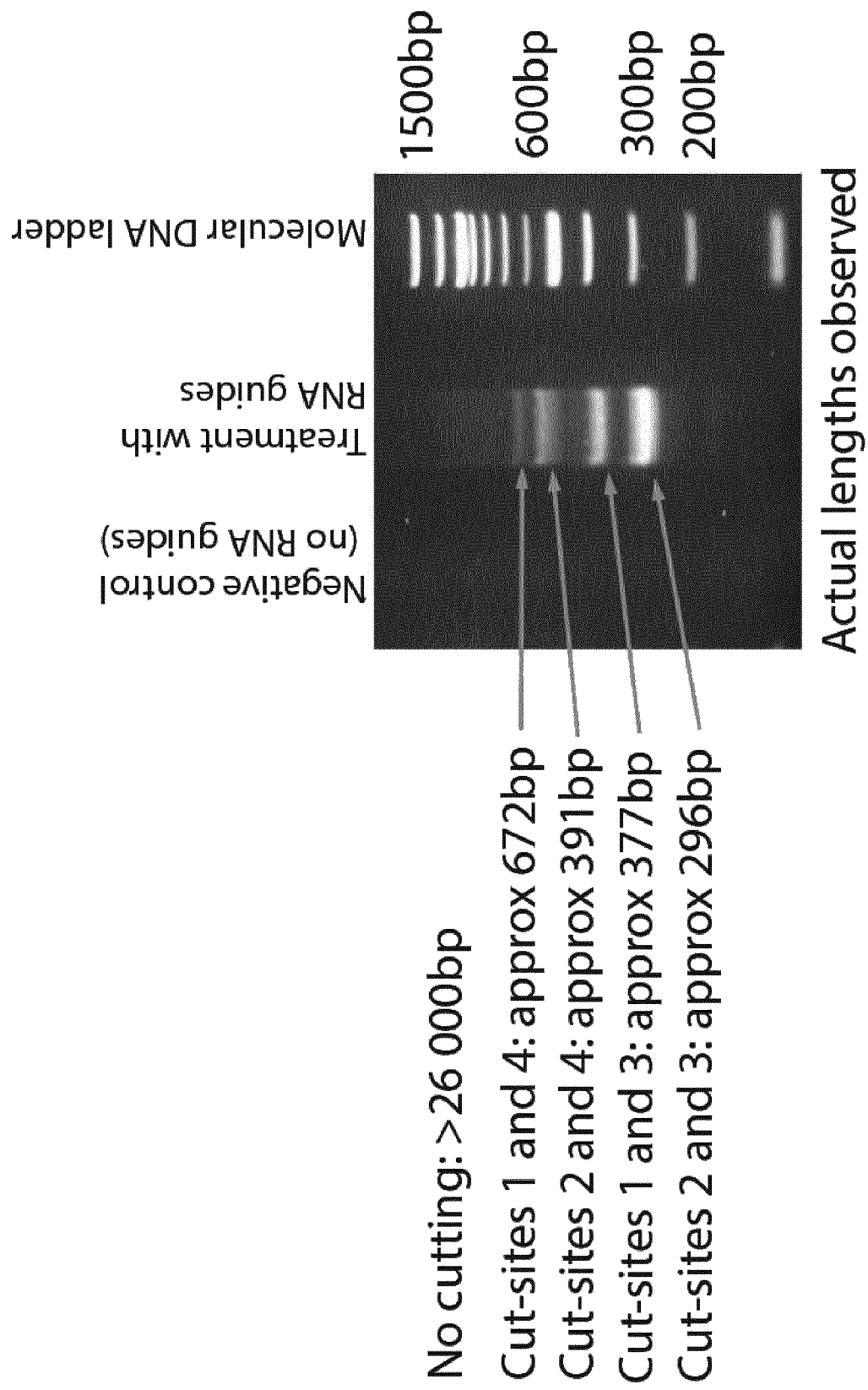
Figure 3C:
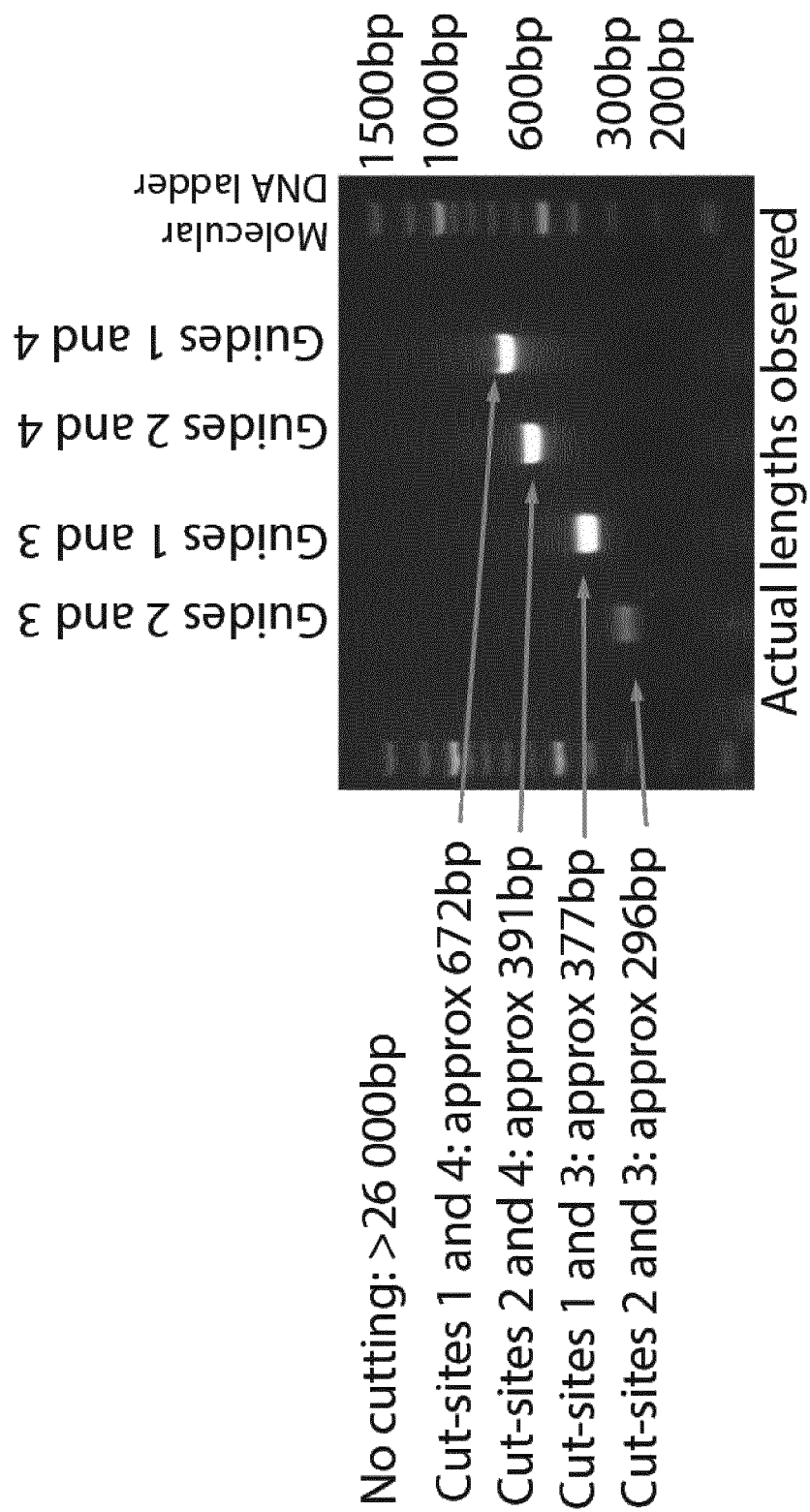

When analysing the size of the PCR product from treated Kasumi-1 cells, it was found that the PCR reaction gave rise to four PCR products of different lengths (FIGS. 3B and 3C). In FIG. 3B two guides on each site of the fusion site were used, wherein in FIG. 3C one guide on each site of the fusion site was used. It was further demonstrated that the sequence of the PCR-products matched with the AML1-ETO sequence minus the excised region.

Conclusion

This example demonstrates that targeting introns placed on either side of the DNA-break site (fusion-site) leads to an excision of the part of the genome flanked by the guides. Further, this example demonstrates that using one guide for each intron or using two guides for each intron leads to such excision.

Example 4—Western Blot Verification of the Method of the Invention

Aim of Study

To verify by Western blot that the method of the invention indeed cuts out of part of the AML1-ETO fusion oncogene thereby preventing expression of the fusion protein.

Materials and Methods

Kasumi-1 cells were treated with AML guides, ETO guides, or both (see example 2). Cells were then lysed and expression of the fusion-oncogene product was assessed by western blotting using an AML1 gene-product specific antibody.

Western Blot:

Four hundred thousand THP-1 cells and one million A549 or HaCat cells were lysed in 100 µL or 60 µL of ice-cold Pierce RIPA lysis buffer (Thermo Scientific) supplemented with 10 mM NaF, 1× complete protease cocktail inhibitor (Roche) and 5 IU·mL$^{-1}$ benzonaze (Sigma), respectively. Protein concentration was determined using a BCA protein assay kit (Thermo Scientific). Whole-cell lysates were denatured for 3 min at 95° C. in presence of 1×XT Sample Buffer (BioRad) and 1×XT reducing agent (BioRad). 10-40 µg of reduced samples were separated by SDS-PAGE on 4-20% Criterion TGX precast gradient gels (BioRad).

Transfer onto PVDF membranes (BioRad) was done using a Trans-Blot Turbo Transfer system for 7 min. Membranes were blocked for 1 h with 5% skim-milk (Sigma Aldrich) at room temperature in PBS supplemented with 0.05% Tween-20 (PBST). Membranes were fractionated in smaller pieces and probed overnight at 4° C. with specific primary antibodies against the AML1 gene-product or against vinculin, which was used as loading control.

Membrane was washed three times and exposed using either the SuperSignal West Pico PLUS chemiluminescent substrate or the SuperSignal West Femto maximum sensitivity substrate (ThermoScientific) and an Image Quant LAS4000 mini imager (GE Healthcare). The levels of proteins were quantified by densitometry using the Image J software.

Results

Figure 4:
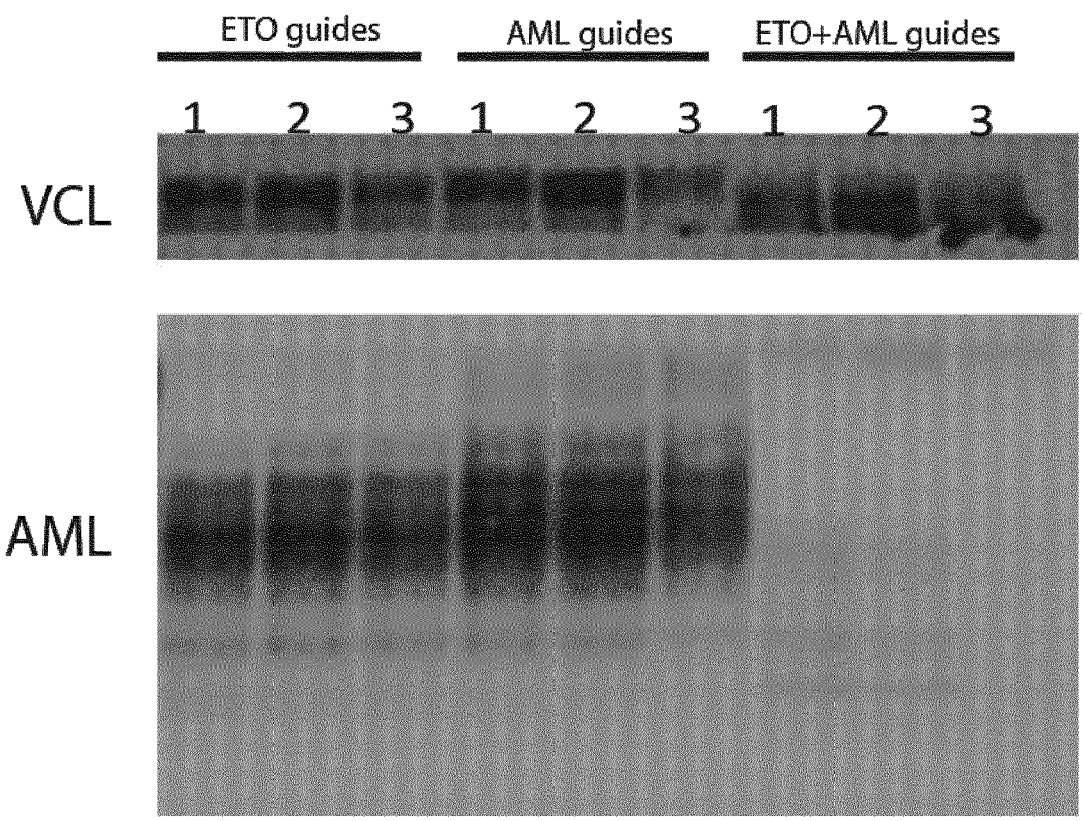
FIG. 4 shows deletion at the genomic level ablates expression of the fusion-oncogene product. Kasumi-1 cells were treated with AML guides, ETO guides, or both. Cells were then lysed and the expression of the fusion-oncogene product was assessed by western blotting using a fusion-gene-product specific antibody.

The results show that only when both AML and ETO specific guides are present, the expression of the fusion gene is removed (FIG. 4).

Conclusion

The presented data show that the method of the invention is able to completely ablate the presence of the fusion protein. On the other hand, if only guides for one of the genes are present, protein expression is still detectable. Thus, these data indicate that the method is specific for the fusion gene AND that they will not harm the expression of AML1 when AML1 and ETO guides are not combined.

Example 5—Other Fusion Gene Related Cancers

Aim of Study

To test if the method is generally applicable for the targeting of fusion-oncogenes.

Methods and Materials

Guides targeting fusion-oncogenes in two other cancer derived cell lines that also have fusion-oncogenes were designed. Non-leukemic cancer-derived cells were selected to test if the method of the invention would also work for other cancer types than leukaemia (as in example 2). Further, in one of the selected cell lines (H2228) the fusion was generated through an inversion instead of a translocation as was the case for both the leukemic cell line (Kasumi) and the second non-leukemic cell line (HCC78).

TABLE 3

| Cell lines: | | | |
|---|---|---|---|
| Cell line | Fusion-oncogene | Rearrangement type | Disease |
| H2228 | EML4-ALK | Inversion (Chr2) | Non-small cell lung carcinoma |
| HCC78 | SLC34A2-ROS1 | Translocation (chr4-chr6) | Non-small cell lung carcinoma |

For each fusion-oncogene two gRNAs for each targeted intron were designed. Flanking primers were designed to detect excision of the appropriate genomic region.

Specific guides used are indicated in table 1. SEQ ID NO: 5-8 for SLC34A2-ROS1 and SEQ ID NO: 9-12 for EML4-ALK.

Screening primers used are indicated in table 3.

TABLE 4

| | Screening primers | | | |
|---|---|---|---|---|
| 17 | SLC34A2 F | 5'-GCCAGTGGAGTAAACAGCACT'3' | SLC34A2 |
| 18 | SLC34A2 R | 5'-CTGAGAAGTTTGGCAATGAGCT-3' | SLC34A2 |
| 19 | ROS1 F | 5'-AGACACTCCTCTCACAGGACTA-3' | ROS1 |
| 20 | ROS1 R | 5'-TTCAACTCCCAAGTTCATGCAC-3' | ROS1 |
| 21 | EML4 F | 5'-GAAGGCAGGAATAACCTAGTC-3' | EML4 |
| 22 | EML4 R | 5'-CCAAGCAGAAGTACGATGATAA-3' | EML4 |
| 23 | ALK F | 5'-AGATGGCAGGAGTGAGGAGT-3' | ALK |
| 24 | ALK R | 5'-GTCCTGTCTGTCTGCTGGAA-3' | ALK |

Cell culturing, electroporation, genomic DNA isolation, PCR and electrophoresis were performed as indicated in example 2.

Results

The two cell lines H2228 and HCC78 (with known fusion-oncogenes) were targeted by the guides. Primers flanking the DNA region targeted by the guides were used for PCR reactions. If the RNA guides mediated cutting, a number of PCR products of four potential different sizes were expected, whereas "no-cutting" would lead to a PCR product to long to amplify.

Figure 5:
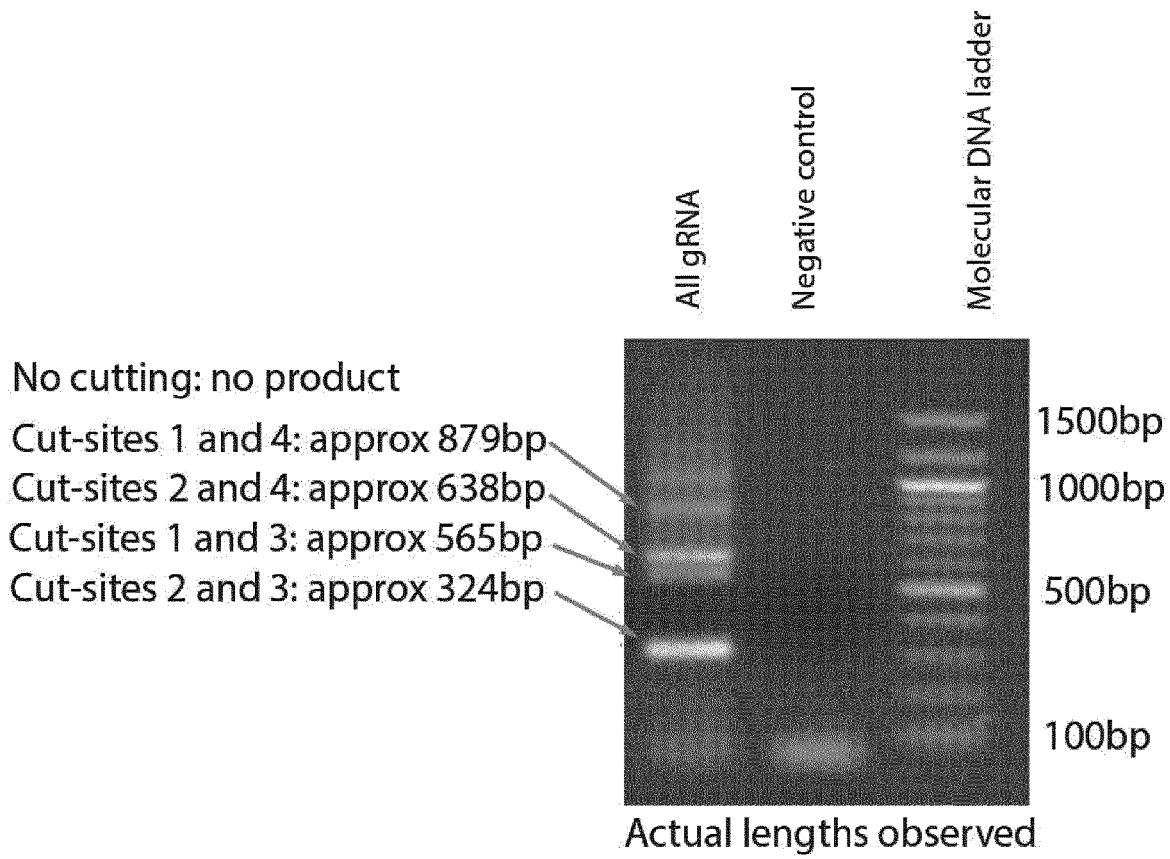
FIG. 5 shows PCR reaction of the two cell lines H2228 and HCC78 after treatment with a complex of guide and RNA-guided endonuclease. A: EML4-ALK fusion oncogene (H2228 cell line). B: SLC34A2 fusion oncogene (HCC78 cell line) (see also text to FIG. 3). The H2228 and HCC78 cells lines are both derived from non-small cell lung cancer (adenocarcinoma) and both harbour important fusion-oncogenes. This experiment demonstrates that our method is able to target other fusion-oncogenes than the AML1-ETO. Further, it demonstrates that our method works in other types of cancer besides AML.
Figure 5:
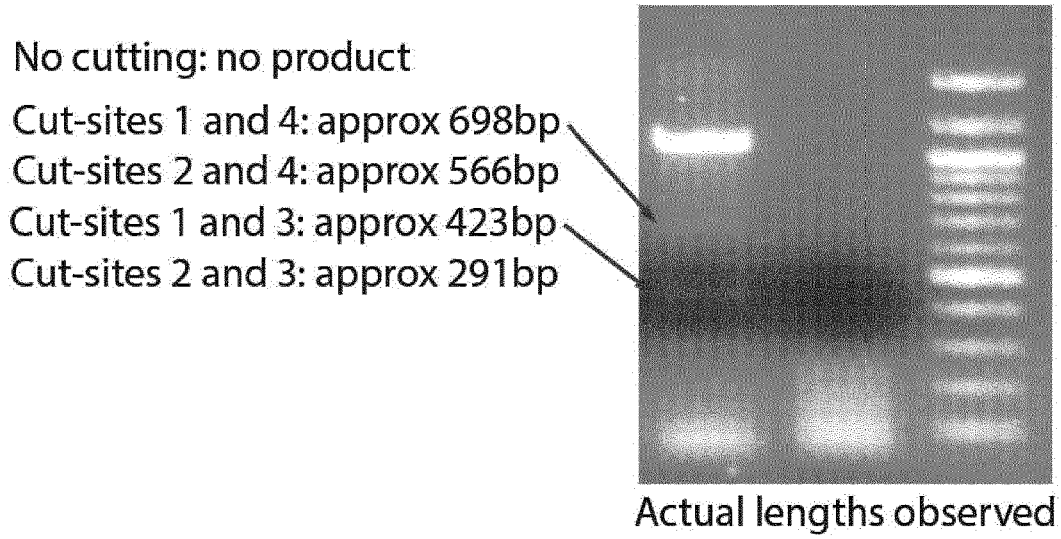

The results presented in FIG. 5A show that for the SLC34A2 fusion oncogene (HCC78 cell line) four PCR bands are clearly visible indicating efficient cleavage of the fusion oncogene. The results presented in FIG. 5B show that for the EML4-ALK fusion oncogene (H2228 cell line) PCR bands are clearly visible indicating efficient cleavage for at least some of the tested guides in these preliminary experiments.

Conclusion

These experiments demonstrate that the method of the invention to target fusion-oncogenes is not specific to AML and the AML1-ETO fusion genes (example 2) nor is it restricted to leukaemia or to fusions generated through specific rearrangement types such as translocations. Rather, the data indicate that the method is applicable in all fusion-oncogenes in all cancer types.

Example 6—Primary Patient Derived Cancer Cells

Aim of Study

To verify by PCR that the method targets fusion genes in patient samples.

Materials and Methods

Figure 6A:
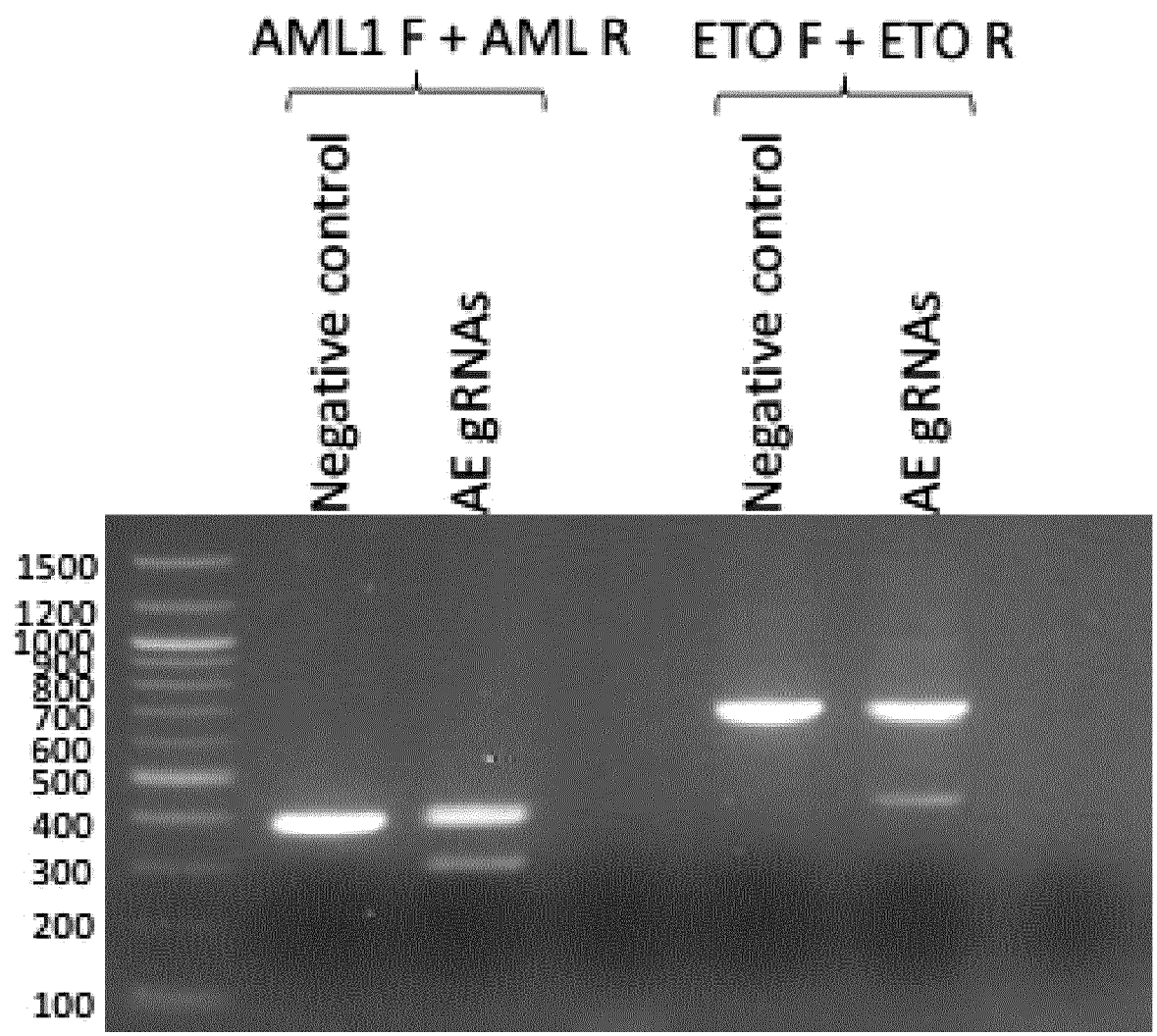
FIG. 6 shows that the invention also works on primary patient derived cancer cells. For this figure, blood leukocytes containing AML cancer cells were harvested from the blood of an AML cancer patient. AML1 and ETO guides (seq ID 1,2,3 and 4) were first tested separately in pairs (seq ID 1 and 2; and seq ID 3 and 4) for efficiency (A) before being used in combination (B). Genomic DNA was then isolated and analysed by PCR using PCR-primers. In (A), the PCR-primers flank the DNA-break site targeted by the RNA-guides at AML1 and ETO genes individually. In (B), the PCR-primers are placed flanking both the AML1 target-site and the ETO target-site. In (B), the four PCR products with different sizes demonstrates that the four guides target the intended regions of the AML1-ETO fusion gene in the primary cancer cells from AML patients.
Figure 6B:
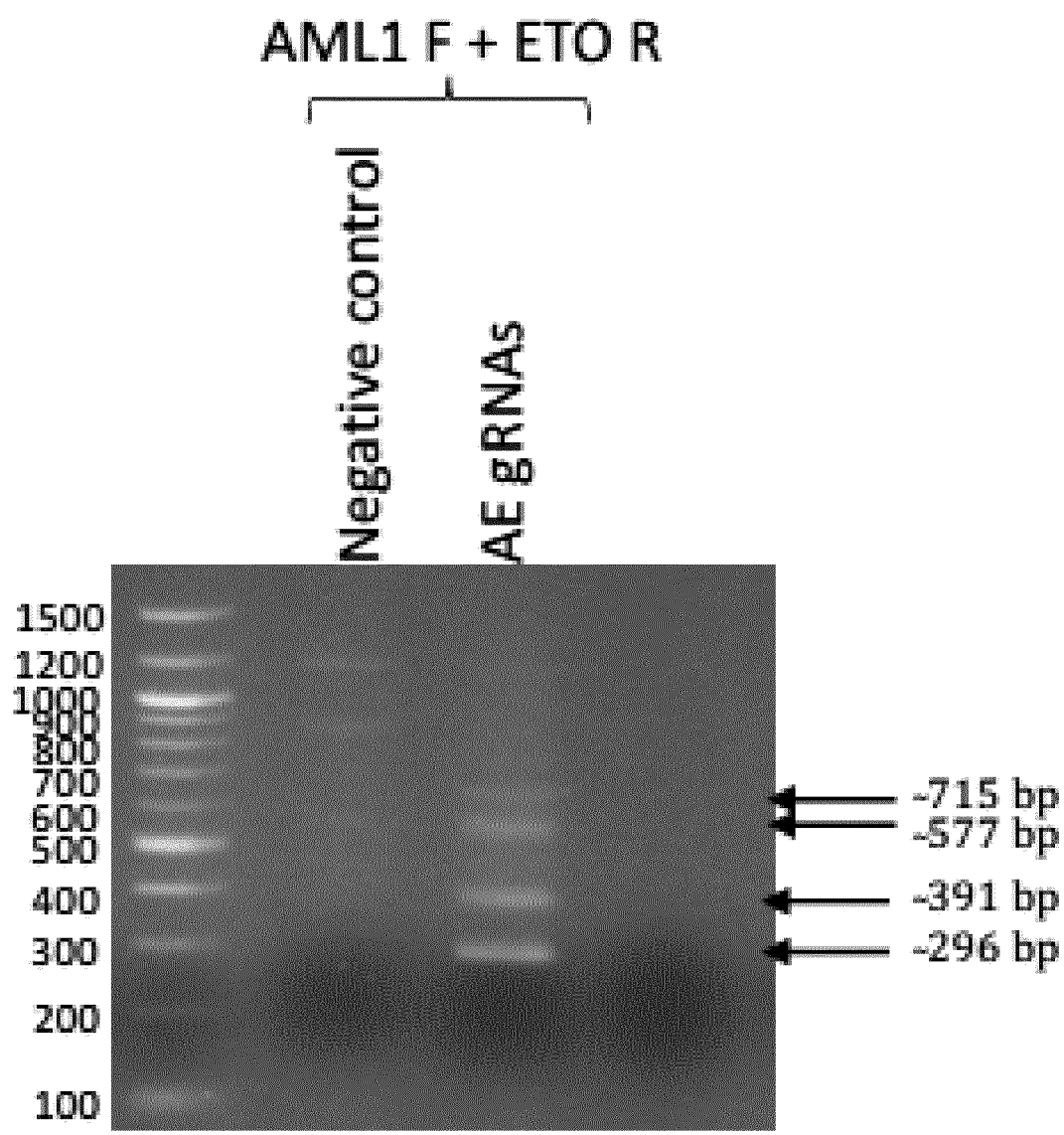

Electroporation:
  See example 2.
Patients:
  The selected patients had previously been identified as have AML1-ETO positive AML. Thus, cancer cells from these patients harbor the AML1-ETO fusion oncogene.
Cell Maintenance:
  Peripheral Blood Mononuclear cells (PBMCs) were isolated from blood of patients using ficoll plaque. Cells were then snap-frozen in freeze-medium containing DMSO. For these experiments, cells were thawed in RPMI growth medium containing 10% Fetal Calf Serum (FCS). Cells were maintained in PRMI+10% FCS for 24 hours before electroporation.
  Day 0: Patient sample was thawed (65% blasts→65% of white blood cells are cancer cells with the AML1-ETO fusion)
  Day 1: Adherent and suspension were pooled and cells were electroporated with RNPs (AML1+ETO gRNAs-cas9 or cas9 alone) using guides with SEQ ID NO's: 1,2, 3 and 4.
  Day 2: Purification of genomic DNA from PBMCs and PCR amplification with AML and ETO primers
Genomic DNA Extraction and PCR:
  See example 3
Guide RNA's:
  The specific guides used are indicated in table 1 as SEQ ID NO's: 1-4.
Results:
  A) In this experiment, guides for AML and for ETO were used separately to test if the guides were efficient in targeting the fusion gene in these primary patient cells. Positive results yield a PCR product smaller than the control, because using two guides for each target leads to cutting out for a portion of the genomic DNA placed between the PCR primers (FIG. 6A).
  B) In this experiment, the AML and ETO primers were combined. Since four RNA-guides were used (two for AML1 and two for ETO), four different PCR products are visible if the fusion-oncogene is successfully targeted by our method (FIG. 6B).
Conclusion:
  The method of the invention targets fusion-oncogenes in primary cancer cells from cancer patients.

Example 7—Xenograft Model of AML

Aim of Study

To verify that the treatment of cancer cells ex vivo leads to a tumor growth inhibition in vivo in a xenograft model of AML.

Materials and Methods

Figure 7:
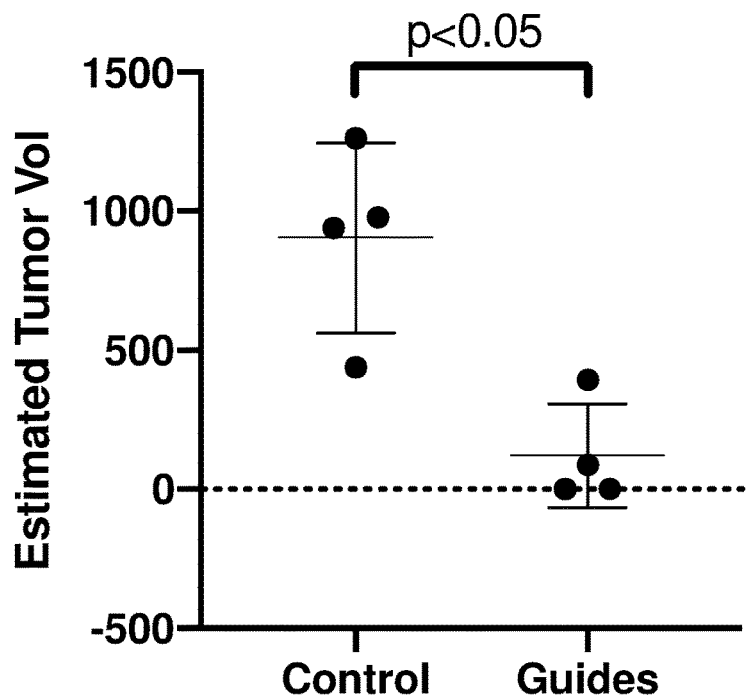
FIG. 7 shows the estimated tumor volume of Kasumi-1 cells injected subcutaneously into the flank of nude mice. Kasumi-1 cells were either treated with Cas9 alone (control) or with Cas9 AND AML1 and ETO guides (seq ID 1,2,3 and 4, Guides). Cells were injected in matrigel.

Electroporation:
  See example 2.
Cell Maintenance:
  See example 2.
Mice:
  For this experiment, immunodeficient nude mice (athymic mice with absent T-cells) were used.
Xenograft:
  Kasumi-1 cells treated with either control Cas9 or with Cas9 in complex with AML1 and ETO guides were injected subcutaneously in the flank of nude mice. Control cells were injected in the left flank and the Kasumi-1 cells treated with Cas9 and AML1 and ETO guides were injected in the right flank. Tumor growth was assessed by estimating tumor volume 4 weeks after time of injected.
  Day 1: Electroporation of kasumi-1 cells with AML1 gRNA 3-cas9+ETO gRNA 2-cas9 (seq ID 1,2,3 and 4; Guides) or cas9 alone (Control)
  Day 3: Electroporated cells were injected into nude mice in matrigel Week 4: Tumor volume was estimated
Guide RNA's:
  The specific guides used are indicated in table 1 as SEQ ID NO's: 1-4.
Results:
  The growth of Kasumi-1 cells treated with the method of the invention was inhibited compared to control treated Kasumi-1 cells in vivo (FIG. 7).
Conclusion:
  The method of inventions inhibits tumor growth in vivo.

The invention claimed is:

1. A composition comprising:
   a first gRNA bound to an RNA-guided endonuclease forming a first ribonucleoprotein complex, wherein said first gRNA comprises a first targeting sequence complementary to a first target sequence in an intron in the 5' region of a fusion oncogene; and
   a second gRNA bound to an RNA-guided endonuclease forming a second ribonucleoprotein complex, wherein said second gRNA comprises a second targeting sequence complementary to a second target sequence in an intron in the 3' region of the fusion oncogene;
wherein said first gRNA comprises a targeting sequence selected from the group consisting of SEQ ID NO: 1-2, 5-6, and 9-10 and said second gRNA comprises a targeting sequence selected from the group consisting of SEQ ID NO: 3-4, 7-8 and 11-12.

2. The composition according to claim 1, wherein the fusion oncogene gene comprises a gene sequence selected from the group consisting of ALK, ROS1, ETO, SLC34A2, EML4, and AML1.

3. The composition according to claim 1,
   wherein the 5' region of the fusion oncogene comprises a gene sequence selected from the group consisting of AML1, SLC34A2, and EML4;
   and/or
   the 3' region of the fusion oncogene gene comprises a gene sequence selected from the group consisting of ETO, AML1, ALK, and ROS1.

4. The composition according to claim 1, wherein the fusion oncogene gene is selected from the group consisting of AML1-ETO, SLC34A2-ROS1, and EML4-ALK.

5. The composition according to claim 1, wherein the first target sequence for the first ribonucleoprotein complex is positioned in one of five introns closest to the fusion site, in the 5' region of the fusion oncogene.

6. The composition according to claim 1, wherein the second target sequence for the second ribonucleoprotein complex, is positioned in one of five introns closest to the fusion site, in the 3' region of the fusion oncogene.

7. The composition according to claim 1, wherein:
   the target sequence for the first ribonucleoprotein complex is positioned in one of the three introns most close to the fusion site, in the 5' region of the fusion oncogene; and
   the target sequence for the second ribonucleoprotein complex is positioned in one of three introns most close to the fusion site, in the 3' region of the fusion oncogene.

8. The composition according to claim 1, wherein the gRNA comprises artificial nucleotides.

9. The composition according to claim 1, wherein the ribonucleoprotein complexes are present, alone or in combination, in a delivery vehicle.

10. A method for treating a subject suffering from a fusion oncogene related cancer, the method comprising administrating to the subject a composition comprising:
    a first gRNA bound to an RNA-guided endonuclease forming a first ribonucleoprotein complex, wherein said first gRNA comprises a first targeting sequence complementary to a first target sequence in an intron in the 5' region of a fusion oncogene; and
    a second gRNA bound to an RNA-guided endonuclease forming a second ribonucleoprotein complex, wherein said second gRNA comprises a second targeting sequence complementary to a second target sequence in an intron in the 3' region of the fusion oncogene;
wherein said first gRNA comprises a targeting sequence selected from the group consisting of SEQ ID NO: 1-2, 5-6, and 9-10 and said second gRNA comprises a targeting sequence selected from the group consisting of SEQ ID NO: 3-4, 7-8 and 11-12.

11. The method according to claim 10, wherein said cancer is a leukemia.

12. The method according to claim 10, wherein said cancer is a leukemia, selected from the group consisting of ALL, AML, APL, CML, lymphoma, PTCL, ALCL and DLBCL.

13. The method according to claim 10, wherein said cancer is a solid cancer.

14. The method according to claim 10, wherein said cancer is a solid cancer selected from the group consisting of lung cancer, sarcoma, glioma, thyroid cancer, melanoma, urothelial cancer, colorectal cancer, breast cancer and lymphoma.

15. An in vitro method for deleting part of a fusion oncogene in a cell, the method comprising contacting the cell with a composition comprising:
    a first gRNA bound to an RNA-guided endonuclease forming a first ribonucleoprotein complex, wherein said first gRNA comprises a first targeting sequence complementary to a first target sequence in an intron in the 5' region of a fusion oncogene; and
    a second gRNA bound to an RNA-guided endonuclease forming a second ribonucleoprotein complex, wherein said second gRNA comprises a second targeting sequence complementary to a second target sequence in an intron in the 3' region of the fusion oncogene;
wherein said first gRNA comprises a targeting sequence selected from the group consisting of SEQ ID NO: 1-2, 5-6, and 9-10 and said second gRNA comprises a targeting sequence selected from the group consisting of SEQ ID NO: 3-4, 7-8 and 11-12.

16. The in vitro method according to claim 15, wherein the partial fusion oncogene deletion by the gRNAs bound to the RNA-guided endonuclease, results in an out-of-frame gene product or a premature stop codon in the remaining fusion oncogene.

* * * * *